United States Patent [19]

Kisilevsky et al.

[11] Patent Number: 5,164,295
[45] Date of Patent: Nov. 17, 1992

[54] METHOD FOR IDENTIFYING AMYLOID PROTEIN-EXTRACELLULAR MATRIX PROTEIN AFFINITY ALTERING COMPOUNDS

[75] Inventors: Robert Kisilevsky; Walter A. Szarek; Suree Narindrasorasak, all of Kingston, Canada

[73] Assignee: The Upjohn Company, Kalamazoo, Mich.

[21] Appl. No.: 665,524

[22] Filed: Mar. 6, 1991

[51] Int. Cl.$^5$ .................... C12Q 1/00; G01N 33/53; G01N 33/566
[52] U.S. Cl. .................... 435/7.8; 435/7.95; 435/7.93; 435/7.92; 436/501
[58] Field of Search .............. 436/501, 503; 435/7.8, 435/7.95, 960, 7.93, 7.92

[56] References Cited

U.S. PATENT DOCUMENTS 4,666,829  5/1987  Glenner et al. .................. 435/6
4,956,347  9/1990  Ban et al. ........................ 514/54
4,958,347  9/1990  Ban et al. ........................ 514/54

OTHER PUBLICATIONS

Perlmutter et al. (1990) Brian Research 508:13–19.
Young et al. (1989) Acta Neuropathol 78:202–209.
Perlmutter et al. (1990) Brian Res. Bull. 24:677–686.
Narindrasorasak et al. (1991) Abstract Only J Biol Chem 266:12878-83.
Perlmutter et al. (1990) Manl. Abstract Only Brain Res Bul 2415 677–686.
Perlmutter et al. (1990 Jan.) Abstract Only Neurology 5084 13–19.
Kang, J. et al., "The precursor of Alzheimer's disease amyloid A4 protein resembles a cell-surface receptor," 1987, Nature, 325: 733–736.
Ponte, P. et al., "A new A4 amyloid mRNA contains a domain homologous to serine proteinase inhibitors," 1988, Nature, 331: 525–527.
Kitaguchi, N et al., "Novel precursor of Alzheimer's disease amyloid protein shows protease inhibitory activity," 1988, Nature, 331: 530–532.
Selkoe, D. J., "Deciphering Alzheimer's disease: The amyloid precursor protein yields new clues," 1990, Science, 248: 1058–1060.
Wurtman, R. J., "Alzheimer's Disease," Scientific American, 252: 62–74.
Glenner, G. G., "The pathobiology of Alzheimer's disease," 1989, Ann. Rev. Med., 40: 45–51.
Müller-Hill, B., "Molecular biology of Alzheimer's disease," 1989, Annu. Rev. Biochem., 58: 287–307.
Price, D. L. et al., "Cellular and molecular biology of Alzheimer's disease," 1989, BioEssays, 10: 69–74.
Snow, A. D. et al., "The presence of heparan sulfate proteoglycans in the neuritic plaques and congophilic angiopathy in Alzheimer's disease," 1988, American Journal of Pathology, 133: 456–463.
Snow, A. D. and Robert Kisilevsky, "Temporal relationship between glycosaminoglycan accumulation and amyloid deposition during experimental amyloidosis," 1985, Laboratory Investigation, 53: 37–44.
Snow, A. D. et al., "A close ultrastructural relationship between sulfated proteoglycans and AA amyloid fibrils," 1987, Laboratory Investigation, 57: 687–698.
Snow, A. D. et al., "Cationic dyes reveal proteoglycans structurally integrated within the characteristic lesions of Alzheimer's disease," 1989, Acta Neuropathol., 78: 113–123.
Young, I. D. et al., "The ultrastructural localization of sulfated proteoglycans is identical in the amyloids of Alzheimer's disease and AA, AL, senile cardiac and medullary carcinoma-associated amyloidosis," 1989, Acta Neuropathol., 78: 202–209.
Snow, A. D. et al., "Sulfated glycosamioglycans: A common constituent of all amyloids?" 1987, Laboratory Investigation, 56: 120–123.
McCubbin, W. D. et al., "Circular–dichroism studies on two murine serum amyloid A proteins," 1988, Biochem. J., 256: 775–783.
Norling, B. et al., "Immunohistochemical identification of heparan sulphate proteoglycan in secondary systemic amyloidosis," 1988, Clin. Exp. Immunol., 73: 333–337.
Kisilevsky, R., "Theme and variations on a string of myloid," 1989, Neurobiology of Aging, 10: 499–500.
Kisilevsky, R., "Heparan sulfate proteoglycans in amyloidogenesis: An epiphenomenon, a unique factor, or the tip of a more fundamental process?" 1990, Laboratory Investigation, 63: 589–591.
Sanes, J. R., "Extracellular matrix molecules that influence neural development," 1989, Ann. Rev. Neurosci., 12: 491–516.
Martin, G. R. et al., "Basement membrane proteins: Molecular structure and function," 1988, 39: 1–50.
McDonald, J. A., "Extracellular matrix assembly," 1988, Ann. Rev. Cell Biol., 4: 183–207.
Klier, F. G. et al., "Amyloid β-protein precursor is associated with extracellular matrix," 1990, Brain Research, 515: 336–342.
Snow, A. D. et al., "Early accumulation of heparan sulfate in neurons and in the beta-amyloid protein-containing lesions of Alzheimer's disease and Down's Syndrome," 1990, American Journal of Pathology, 137: 1253–1270.
Margolis, R. U. and R. K. Margolis, "Properties of nervous tissue proteoglycans relevant to studies on Alzheimer's disease," 1989, Neurobiology of Aging, 10: 500–502.

(List continued on next page.)

Primary Examiner—Christine M. Nucker
Assistant Examiner—David R. Preston
Attorney, Agent, or Firm—Mark DeLuca

[57] ABSTRACT

A method for identifying compounds useful for treating patients with amyloidosis is disclosed. Compounds are screened according to the present invention to determine their ability to modulate the affinity between amyloid protein and proteins of the extracellular matrix.

4 Claims, No Drawings

OTHER PUBLICATIONS

Caputo, C. B., "What is the significance of the binding of proteoglycans to amyloid"? 1989, Neurobiology of Aging, 10: 503-504.

Schubert, D. "The biological roles of heparan sulfate proteoglycans in the nervous system," 1989, Neurobiology of Aging, 10: 504-506.

Benditt, E. P., "What role(s) may extracellular matrix, particularly heparan sulfate, play in amyloid of Alzheimer's disease," 1989, Neurobiology of Aging, 10: 506.

Linker, A., "Proteoglycans in the pathogenesis of amyloidosis," 1989, Neurobiology of Aging, 10: 507-508.

Shirahama, T., "Proteoglycans in Amyloidogenesis," 1989, Neurobiology of Aging, 10: 508-510.

Snow, A. D. and T. N. Wight, 1989, Neurobiology of Aging, 10: 510-512.

METHOD FOR IDENTIFYING AMYLOID PROTEIN-EXTRACELLULAR MATRIX PROTEIN AFFINITY ALTERING COMPOUNDS

FIELD OF THE INVENTION

The present invention relates to a method of identifying compounds which impair and/or prevent initiation and/or progression of amyloid deposition, such compounds being useful as therapeutics for treating amyloidosis and amyloid-related disorders.

BACKGROUND OF THE INVENTION

Amyloidosis is the pathological condition defined as the accumulation in tissues of an amyloid protein, usually in an amount sufficient to impair normal organ function. Several different forms of amyloid protein have been defined and at least six different amyloidosis conditions have been described including: amyloidosis related to Alzheimer's disease, amyloidosis related to inflammation, amyloidosis related to adult onset diabetes, amyloidosis related to Gerstmann Straussler Syndrome and Creutzfeldt-Jakob disease, amyloidosis related to familial amyloidotic polyneuropathy, and amyloidosis related to hereditary cerebral hemorrhage with amyloid. Amyloid is also associated with multiple myeloma, Hodgkin's disease, tumors, familial Mediterranean fever as well as generally in aging and other familial forms.

Amyloidosis generally manifests itself as the deposition and accumulation of an amyloid protein in tissues in the form of fine fibrils thereby forming histologic entities such as plaques, or "amyloid tumors". Although amyloids are classified by type of protein, two major clinical forms of amyloidosis are recognized. Primary amyloidosis is defined as amyloidosis where there is no associated disease; secondary or acquired amyloidosis is amyloidosis associated with chronic diseases such as infectious or inflammatory diseases.

In primary amyloidosis, amyloid fibril deposits or "amyloid tumors" can be found in all of the various organs and tissues of the body. Depending on their localization, fibril deposits of primary amyloidosis determine the severity of the implications associated with the condition.

In secondary amyloidosis, the occurrence of amyloid fibril deposits can take place throughout the body in all organs and tissues. In some cases, the amyloid is found associated with only one organ. For example: in Alzheimer's disease-related amyloidosis, amyloid plaques are primarily detected in brain; in amyloidosis associated with adult onset diabetes mellitus, amyloid deposits are often localized only in the pancreas. Nevertheless, amyloid deposits are often found throughout the body in secondary amyloidosis. In particular, in amyloidosis associated with tumors, the occurrences of amyloid deposits are found in nontumourous organs as well as in areas where malignancies are present.

Amyloidosis can only be diagnosed by biopsy. However, the appearance of various symptoms and signs described above lead one to suspect the presence of amyloidosis either as a primary or secondary form.

Local amyloid deposits can be removed without recurrence. However, the occurrence of amyloid deposits in various organs can cause severe problems in the normal functioning of the affected organs. Myocardial amyloidosis is a common cause of death primarily due to arrhythmias or intractable cardiac failure. All forms of renal amyloidosis carry a poor prognosis. Amyloidosis associated with malignancies have the poorest prognosis. In the case of Alzheimer's disease, it is believed that the severity of the disease itself may be reduced by the elimination or slowing of the progression of amyloidosis localized in brain tissue. In some secondary amyloidosis, successful treatment of the underlying disease can reduce or eliminate the presence of amyloidosis.

Treatment for primary amyloidosis is currently directed at controlling the symptoms which are caused by the lesions. Similarly, treatment in secondary amyloidosis attempts to alleviate the problems caused by the lesions as well as treatment of the underlying disease. There is, however, no therapy to reduce or eliminate amyloid deposits. Furthermore, there are currently no assays which are useful to identify compounds that can prevent, slow or reverse the deposition or accumulation of amyloid. Identification of such compounds could provide potential therapeutics for amyloidosis.

The present invention is directed at providing a method of identifying compounds which prevent or impair the initiation of amyloid deposition and to slow down and reverse the accumulation of amyloid in amyloid deposits. According to the present invention, an assay is provided which can be used to identify compounds which lower the affinity of amyloids and/or amyloid precursor proteins to each other and to nonamyloid proteins or proteoglycans associated with amyloid deposition. Compounds identified by the present invention can be useful in the treatment of patients suffering from primary amyloidosis as well as patients who are suffering secondary amyloidosis in association with another disease because they can interfere with critical events necessary for amyloid deposition, specifically the nucleation events of amyloid protein binding to extracellular matrix proteins (EMP). The present invention provides a method useful in the discovery of drugs for the prevention and treatment of amyloidosis, amyloidosis-related diseases and for the prevention and treatment of tissue destruction associated with amyloid accumulation by providing a method of identifying compounds which impair the binding interactions.

In some cases, such as Alzheimer's disease (AD), the treatment of the amyloidosis secondary to the disease can be useful in improving the prognosis of the patient by counteracting secondary effects of primary disease itself. Accordingly, the present invention provides a method which can identify compounds useful in the treatment of Alzheimer's disease.

According to the present invention, a method is provided which can evaluate a compound's ability to lower the affinity of Alzheimer's amyloid precursor protein (AAP) to proteins or proteoglycans found in the extracellular matrix of brain tissue. By providing a method of identifying compounds which affect the binding of AAP to EMP, the present invention is useful in identifying compounds which can prevent or impair the nucleation of amyloid. Thus, compounds can be identified which specifically affect an event linked with the onset of a pathological condition associated with Alzheimer's disease. By specifically modulating the affinity between AAP and EMP, the binding of AAP to EMP can be reduced or inhibited and formation of amyloid deposits which are commonly found in patients with Alzheimer's disease can be avoided.

INFORMATION DISCLOSURE

U.S. Pat. No. 4,956,347, issued Sep. 11, 1990 to Ban et al. relates to the use of a mixture of "sulfomucopolysaccharides" comprising heparin, heparan sulfate-like substance, dermatan sulfate, and chondroitin sulfate A and C, for the treatment of patients suffering from Alzheimer's-type senile dementia.

Kang, J., et al., "The precursor of Alzheimer's disease amyloid A4 protein resembles a cell-surface receptor", Nature, Vol. 325, Feb. 19, 1987, pp. 733-736, report the isolation and sequence of a full length cDNA clone encoding a 695-residue precursor of the amyloid proteins subunit A4, also referred to as $AAP_{695}$.

Ponte, P., et al., "A new A4 amyloid mRNA contains a domain homologous to serine proteinase inhibitors", Nature, Vol. 331, Feb. 11, 1988, pp. 525-527, disclose a novel gene encoding AD protein. The novel precursor is longer than the $AAP_{695}$. It contains an additional 168 base-pair insert, encoding a 56 amino acid domain within the so-called extracellular region of the protein. This protein is referred to as $AAP_{751}$.

Kitaguchi, N., et al., "Novel precursor of Alzheimer's disease amyloid protein shows protease inhibitory activity", Nature, Vol. 331, Feb. 11, 1988, pp. 530-532, report a novel precursor of the amyloid protein A4. This precursor is longer than $AAP_{751}$. It contains an additional 57 base pairs encoding a 19 amino acid domain of unknown function, inserted immediately C-terminal to the insert in $AAP_{751}$. This protein is referred to as $AAP_{770}$.

Selkoe, D. J., "Deciphering Alzheimer's Disease: The Amyloid Precursor Protein Yields New Clues", Science, Vol. 248, pp. 1058-1060, provides a review of AAP genes and proteins. It is reported that the gene occurs in three forms, $AAP_{695}$ $AAP_{751}$, and $AAP_{770}$ and a discussion of the conversion from precursor to the amyloid $\beta$-protein is included.

Wurtman, R. J., "Alzheimer's Disease", Scientific American 252:62-74, provides a review of six hypotheses which underlie the current focus on research on AD. The abnormal protein model that is reported discusses the presence of amyloid deposits in the brains of patients afflicted with Alzheimer's disease.

Glenner, G. G., "The Pathobiology of Alzheimer's Disease", Ann. Rev. Med. 40:45-51 (1989), provides a review of the pathology of AD. The role of the $\beta$-protein as the major component of amyloid fibrils of plaques and cerebral vessels and the paired helical filaments of neurofibrillary tangles is discussed.

Muller-Hill, B. et al., "Molecular Biology of Alzheimer's Disease", Annu. Rev. Biochem., 58:287-307 (1989), provide a review of the molecular biology of Alzheimer's disease. A discussion of the genes encoding the $\beta$-protein, referred to as A4 amyloid, is included. Additionally, the cDNAs of AAP protein, the genes encoding AAP protein, and the link of the AAP protein with AD are discussed.

Price, D. L. et al., "Cellular and Molecular Biology of Alzheimer's Disease", BioEssays, Vol. 10, Nos. 2 and 3, February-March 1989, pp. 69-74, provide a review of the cellular and molecular biology of Alzheimer's disease. Included is a discussion of the animal models presently being used.

Snow, A. D., et al., American Journal of Pathology, Vol. 133, No. 3, December 1988, disclose the presence of heparan sulfate proteoglycan (HSPG) in neuritic plaques associated with Alzheimer's disease. HSPG was detected in the amyloid fibrils present in neuritic plaques in the brains of Alzheimer's patients using antibodies against the protein core of HSPG. Additionally, HSPG was shown to be present in primitive plaques. It is suggested that the accumulation of HSPG in plaques takes place during early stages of plaque development.

Snow, A. D., and Kisilevsky, R., Laboratory Investigation, Vol. 53, No. 1, pp. 37-44 (1985), report the temporal relationship between glycosaminoglycan (GAG) accumulation and amyloid deposition during experimental amyloidosis. Using models which facilitate induction of amyloidosis, it was disclosed that amyloid-associated GAG's appear in the tissues together with the AA amyloid protein independent of the tissue type. It is suggested that the appearance of GAG in the inflammatory amyloidosis condition appears to be part of the process involved in the deposition of the AA protein.

Snow, A. D., et al., Laboratory Investigation, Vol. 57, No. 6, pp. 687-698 (1987) refer to a close structural relationship between sulfated proteoglycans and AA amyloid fibrils. It is disclosed that HSPG is present in amyloid deposits associated with amyloidosis in the spleen and liver. The relationship between the sulfated proteoglycans and AA amyloid fibrils suggests that the proteoglycans have a role in the pathogenesis of amyloidosis. However, the role of the proteoglycans in amyloidosis is reported to be unknown.

Snow, A. D., et al., Acta Neuropathol. 78:113-123 (1989) disclose specific ultrastructural localization of proteoglycans within the characteristic lesions of Alzheimer's disease.

Young, I. D., et al., Acta Neuropathol. 78:202-209 (1989) disclose that the ultrastructural localization of sulfated proteoglycans is identical in the amyloid plaques of Alzheimer's disease, inflammation-associated amyloidosis, immunoglobulin light chain, senile cardiac and medullary carcinoma-associated amyloidoses. In addition to the Alzheimer's amyloid fibrils, amyloid fibrils which contain any one of four unrelated types of amyloid—AA (inflammation-associated), AL (immunoglobulin light chain), senile cardiac (prealbumin) and medullary carcinoma-associated amyloid (procalcitonin)—showed an identical pattern of localization of highly sulfated proteoglycan at the different amyloid fibrils. It is suggested that the constant close spatial relationship between proteglycans and diverse amyloid proteins suggests that proteoglycans play a role in amyloidogenesis.

Snow, A. D., et al., Laboratory Investigation, Vol. 56, No. 1, pp. 120-123 (1987) disclose that sulfated glycosaminoglycans are associated with amyloid deposits regardless of the nature of the amyloid protein reported. It is suggested that the sulfated glycosaminoglycans can influence the folding of diverse amyloid proteins such that all forms of amyloid in amyloid deposits show a significant $\beta$-pleated sheet component and that new therapeutic strategies can be directed toward disrupting this protein-folding activity in an effort to inhibit ongoing amyloid deposition.

McCubbin, et al., Biochem. J., 256:775-783 (1983) discloses that heparan sulfate as opposed to other glycosaminoglycans can significantly increase the $\beta$-sheeting of $SAA_2$ the specific precursor of AA amyloid.

Norling, B., et al., Clin. Exp. Immunol., 73, pp. 333-337 (1988), refers to immunohistochemical identification of HSPG in secondary systemic amyloidosis. The distribution of proteoglycans in kidneys from patients with secondary (AA) systemic amyloidosis were investigated and it is disclosed that HSPG was the only proteoglycan found to be specifically localized in the amyloid deposits. The possible role of HSPG in the pathogenesis of amyloid deposit is discussed. The heterologous nature of protein AA due to differential processing of the precursor molecule SAA is discussed and the possibility of some protein AA forms being positively charged is noted. It is suggested that the positively charged protein AA molecules could hypothetically bind to the highly ionic HSPG molecules in tissues and that such an AA-HSPG complex could serve as a nidus for fibril formation. It is noted that further studies on binding between proteoglycans and amyloid proteins are necessary in order to deduce whether the carbohydrate or protein moiety of HSPG are responsible for localization of amyloid deposits.

Kisilevsky, R., Neurobiol. Aging 10, pp. 499-500 (1989), discloses that, based on theoretical considerations, there are three potential binding sites on $AAP_{770}$ for glycosaminoglycans.

Kisilevsky, R., Laboratory Investigation, Vol. 63, No. 5, pp. 589-591 (1990) reviews a host of possible roles HSPG plays in amyloidogenesis. A review of amyloid-HSPG interaction is provided and there is a discussion of the possible mechanism which gives rise to the presence of both amyloid and HSPG in amyloid plaques.

Sanes, J. R., Ann. Rev. Neurosci., 12:491-516 (1989) provides a review of the extracellular matrix molecules that influence neural development.

Martin, G. R., et al., Advances in Protein Chemistry, Vol. 39, pp. 1-50 provide a review of basement membrane proteins. The components of the basement membrane are discussed, especially at pages 6-33, with particular emphasis on type IV collagen, laminin, and heparan sulfate proteoglycan. The molecular structure and function of the basement membrane proteins is discussed.

McDonald, J. A., Ann. Rev. Cell Biol., 4:183-207 (1988) provides a review of the extracellular matrix assembly. This review primarily discusses the assembly of fibronectin.

Klier, F. G., et al., Brian Research, 515, pp. 336-342 (1990) disclose the ultrastructural distribution of Alzheimer's amyloid precursor in cultured cells. The association of Alzheimer's amyloid precursor to the extracellular matrix protein secreted by the cells is reported.

Snow, A. D., et al., Am. Journal of Pathology, Vol. 137, No. 5, pp. 1253-1270 (November 1990) refer to the accumulation of heparan sulfate in neurons and in the $\beta$-amyloid protein-containing lesions of Alzheimer's disease and Down's syndrome. An immunohistochemical analysis of Alzheimer's and Down's brains with an antiserum to a glycosidic linkage prevalent in heparan sulfate GAGs is provided. It is reported that heparan sulfate is found at the sites of the earliest amyloidotic lesions in young Down's brains, suggesting that HSPG accumulation may occur concurrently with or before amyloid is deposited. It is suggested that AAP and HSPG may play a role in the ultimate formation of fibrillary amyloid.

Margolis, R. U., and Margolis, R. K., Neurobiology of Aging, Vol. 10, pp. 500-502 (1989) disclose various properties of nervous tissue proteoglycans with respect to their proposed relation to amyloid $\beta$-protein in Alzheimer's disease-related amyloidosis. It is pointed out on page 501, column 1, lines 4 to 8 that the role of proteoglycans in Alzheimer's disease amyloidosis is only circumstantial and the role of proteoglycans in it is unclear. At page 502, column 2, lines 3 to 6, it is disclosed that due to the absence of firm evidence specifically linking proteoglycans to pathogenesis of Alzheimer's disease, it is premature to speculate the relationship of proteoglycans to amyloid in degenerative process.

Caputo, C. B., Neurobiology of Aging, Vol. 10, pp. 503-504 (1989) refers to the significance of binding of proteoglycans to amyloid. It is disclosed that colocalization of proteoglycans with amyloids indicates that they are binding but the consequence of such binding is unknown. The question is asked of whether proteoglycans bind inadvertently to amyloid or whether the proteoglycans in binding to amyloid or its precursors lead to the formation of $\beta$-pleated sheet conformation or the stabilization of such a conformation. It is suggested that in vitro studies be performed to determine whether Alzheimer amyloid precursor binds to proteoglycans. On page 503, column 1, last paragraph, the possibility that amyloid protein binds well to proteoglycans is raised. However, evidence is referred to which indicates otherwise.

Schubert, D., Neurobiology of Aging, Vol. 10, pp. 504-506 (1989) refers to the biological roles of heparan sulfate proteoglycans in the nervous system. The relationship of HSPG in Alzheimer's amyloidosis is discussed. Page 505, section 3) asks the question, can APBB (Alzheimer's amyloid protein-AAP) bind to heparin. Evidence is presented which indicates that AAP can bind to heparin. However, the AAP heparin binding is reported to be relatively weak and while it is suggested that HSPG might bind better than heparin to AAP, explaining the colocalization of HSPG and amyloid, no evidence is provided to support that.

Benditt, E. P., Neurobiology of Aging, Vol. 10, p. 506 (1989) refers to what role(s) may extracellular matrix, particularly heparan sulfate, play in amyloid of Alzheimer's disease. On page 506, column 1, lines 12 to 14, it is stated that the suggestion that the heparan sulfate proteoglycans serve as a nidus for plaque development does not seem to fit. A discussion follows putting forth reasons why it is unlikely that HSPG binding to AAP initiates amyloid plaque formation.

Linker, A., Neurobiology of Aging, Vol. 10, pp. 507-508 (1989) discusses proteoglycans in the pathogenesis of amyloidosis. On page 507, column 2, line 17 it is stated that it is legitimate to assume that the presence of GAGs in amyloid deposits imply significance but the specific part played by proteoglycans in amyloid deposition or stabilization is somewhat elusive.

Shirahama, T., Neurobiology of Aging, Vol. 10, pp. 508-510 (1989) refers to proteoglycans in amyloidogenesis. The potential role of proteoglycans and GAGs is discussed and the various theories of amyloidogenesis are reviewed. The likely possibilities of the role of proteoglycans and GAGs in amyloid fibrilogenesis are listed and include as one of three possibilities to influence the localization of amyloid deposits by attracting amyloid to tissue when proteoglycans are present. It is noted that further studies are needed before any clear understanding can be made.

Snow, A. D., and Wight, T. N., Neurobiology of Aging, Vol. 10, pp. 510-512 (1989) discuss comments made in references in Neurobiology of Aging, Vol. 10, pp. 499-510 (1989). In particular, on page 511, column 2, last paragraph they note that it will be important to determine the mode of binding between HSPG and Alzheimer's precursor protein. They discuss specifically that although Alzheimer's precursor protein binds to heparin, the extrapolation that heparan sulfate will also bind to Alzheimer precursor protein must be made cautiously. Further, GAG protein binding models are often unpredictable. It is noted, however, that some preliminary evidence suggests that the β-amyloid protein binds to HSPG. This evidence includes the apparent binding of β-amyloid protein with high molecular weight HSPG in an affinity column. It is suggested that this evidence implies that HSPG and amyloid deposits may be due to the binding affinity of amyloid to HSPG. However, no clear understanding exists at this time.

SUMMARY OF THE INVENTION

The present invention provides a method for identifying compounds useful for treating patients with amyloidosis comprising the steps of contacting a sample of amyloid protein with a sample of an extracellular matrix protein in the presence of a test compound and then determining the binding affinity of the amyloid to the extracellular matrix protein.

DETAILED DESCRIPTION

The present invention provides a method of identifying compounds which modulate the affinity of amyloids to extracellular matrix proteins.

As used herein, the term "amyloid" refers to amyloid proteins, amyloid precursor proteins, intermediates, and modifications and fragments thereof. Amyloids as defined herein constitute components of amyloid plaques. Examples of amyloid include: β-protein associated with Alzheimer's Disease, Down's Syndrome, HCHWA-Dutch type, Guamanian Parkinsonian Dementia Complex and normal aging; the several forms of Alzheimer's precursor protein (AAP: $AAP_{695}$, $AAP_{751}$, and $AAP_{770}$); modified forms of Alzheimer's precursor protein (AAP/s: $AAP_{695}/s$, $AAP_{751}/s$, and $AAP_{770}/s$); Amyloid A (AA), the amyloid associated with inflammation; IAPP, the amyloid associated with adult onset diabetes; prion amyloids, the amyloids associated with Gerstmann Straussler Syndrome and Creutzfeldt-Jakob disease; transthyretin amyloid, the amyloid associated with familial amyloidotic polyneuropathy; and cystatin C, the amyloid associated with Icelandic-type familial hereditary cerebral hemorrhage with amyloid, HCHWA-Icelandic type.

As used herein, the terms "extracellular matrix proteins" and "EMP" refer to the proteins which occur in tissues with which amyloids bind. The binding of amyloids to EMP is believed to be a critical nucleation event which initiates amyloid deposition and accumulation. One feature common to all amyloid deposits is the presence of highly sulfated glycosaminoglycans (GAGs); highly sulfated GAGs have been demonstrated in all forms of amyloid deposits examined to date. GAGs represent the carbohydrate portion of proteoglycans. Ultrastructural analysis has revealed that these GAGs are closely associated with fibril structure, but are not covalently linked to the associated amyloid peptides believed to be responsible for the amyloid fibrils. This conclusion is based on the behavior of amyloid fibrils in denaturing media, such as high concentrations of guanidine or urea, in which the fibril structure is disrupted and the amyloid peptide and the proteoglycan can be dissociated. Where it has been possible to identify the proteoglycan, the basement membrane form of heparan sulfate proteoglycan (HSPG) has emerged as the common element. This has been shown in at least five different amyloidoses, including the AA amyloid related to inflammation, IAPP amyloid in adult onset diabetes, β-amyloid in Alzheimer's disease, the prion amyloids in Gerstmann Straussler Syndrome, Creutzfeldt-Jakob disease and experimental scrapie, and prealbumin amyloid in familial amyloidotic polyneuropathy. In each of these cases the amyloid proteins are clearly unrelated. Ultrastructurally, heparan sulfate or HSPG has been shown to be an integral part of amyloid fibrils. A high degree of β-sheeting is a common characteristic of all amyloids. It has previously been shown that $SAA_2$, the precursor to the AA-type amyloid takes on a much greater degree of β-sheeting in the presence of heparan sulfate when compared to several other GAGs. Thus, in addition to being a common structural component of various amyloids, the HSPG may also exert an effect on the folding of amyloid peptides or their precursors. Furthermore studies of the AA amyloid in experimental animal models have shown that the AA protein and HSPG are deposited coincidentally, regardless of the induction protocol used, or tissue site involved. These results suggest that the basement membrane form of HSPG may be mechanistically involved in general amyloidogenic processes. More generally, the basement membrane is composed of proteins which comprise the extracellular matrix. The present invention discloses that HSPG binds to various forms of amyloid. In addition to HSPG's association with amyloids, other EMPs also bind with amyloids. Examples of EMPs include: heparan sulfate proteoglycan (HSPG); HSPG core protein, that is, the core protein produced by removal of the carbohydrate moiety of HSPG; fibronectin; laminin; and collagen type IV.

As used herein, the terms "binding affinity" and "affinity" refer to the level of attraction between molecular entities. Affinity can be expressed quantitatively as a dissociation constant (Kd), or its inverse, the association constant (Ka).

According to the present invention, either amyloid or EMP is immobilized, and the other of the two is maintained as a free entity. The free entity is contacted with the immobilized entity in the presence of a test compound for a period of time sufficient to allow binding of the free entity to the immobilized entity, after which the unbound free entity is removed. Using antibodies which recognize the free entity, or other means to detect the presence of bound components, the amount of free entity bound to immobilized entity can be measured. By performing this assay in the presence of a series of known concentrations of test compound and, as a control, the complete absence of test compound, the effectiveness of the test compound to impede binding of free entity to immobilized entity can be determined and a quantitative determination of the effect of the test compound on the affinity of free entity to immobilized entity can be made. By comparing the binding affinity of the amyloid-EMP complex in the presence of a test compound to the binding affinity of the amyloid-EMP complex in the absence of a test compound, the ability of the test compound to modulate the binding can be determined.

In the case in which the amyloid is immobilized, it is contacted with free EMP in the presence of a series of concentrations of test compound. As a control, immobilized amyloid is contacted with free EMP in the absence of the test compound. Using a series of concentrations of EMP, the dissociation constant (Kd) or other indicators of binding affinity of amyloid-EMP binding can be determined. In the assay, after the EMP is placed in contact with the immobilized amyloid for a sufficient time to allow binding, the unbound EMP is removed. Subsequently, the level of EMP-amyloid binding can be observed. One method uses anti-EMP antibodies to detect the amount of EMP bound to the amyloid or the amount of free EMP remaining in solution. This information is used to determine first qualitatively whether or not the test compound can prevent or reduce binding between EMP and amyloid. Secondly, the data collected from assays performed using a series of test compound at various concentrations, can be used to measure quantitatively the binding affinity of the EMP-amyloid complex and thereby determine the effect of the test compound on the affinity between EMP and amyloid. Using this information, compounds can be identified which modulate the binding of EMP to amyloid and thereby prevent or reduce the initiation of amyloid deposition and the subsequent development of amyloidosis.

Similarly, the method can be employed using immobilized EMP in contact with free amyloid protein. In this embodiment, anti-amyloid antibodies are used to evaluate qualitatively and quantitatively a test compound's capacity to effect the affinity of free amyloid to immobilized EMP. Thus, using this embodiment, drugs can be developed which modulate the binding of amyloid to EMP thereby either preventing or reducing the initiation of amyloid deposition or the accumulation of amyloid which leads to plaque formation.

The preferred embodiment of the present invention provides a method of identifying compounds potentially useful in the treatment of Alzheimer's disease (AD). The compounds that can be identified using the preferred embodiment of the present invention are useful as in treating AD by impairing the progression of amyloidosis associated with AD in the brains of Alzheimer's patients. There is increasing evidence in the literature that amyloid deposition is an early, if not the primary, event in AD pathogenesis. It is believed that interference with amyloid deposit formation can provide an effective therapy in the treatment of patients suffering from Alzheimer's disease. The present invention relates to a method of identifying compounds that interfere with the process of amyloid deposition by lowering the affinity of Alzheimer's amyloid precursor protein (AAP) to EMPs such as HSPG, laminin and collagen type IV, preferably HSPG. The specific binding affinity of HSPG to AAP disclosed here demonstrates the interaction between the entities that are subsequently found in developed and primitive amyloid plaques. Data indicate that AAPs also have very high affinities for laminin, and interactions between AAP and collagen type IV have been recently reported (Breen, K. C., Society for Neuroscience Abstracts, No. 322.9, p. 787 (1990)). This binding of AAPs to HSPG, laminin, and collagen type IV reflect a general affinity of AAPs for the extracellular matrix proteins. If compounds can be found which modulate the affinity between AAP and EMP, the nucleation event which leads to amyloid plaque formation can be controlled and the amyloidosis condition can be avoided or its severity reduced.

The amyloid protein associated with AD is amyloid $\beta$-protein, a 42–43 amino acid protein that is originally expressed as a precursor protein. Three different forms of precursor proteins have been identified. The dominant form in brain tissue is produced by translation of mRNA encoding a 695 amino acid polypeptide ($AAP_{695}$). Two other forms have also been described: one contains 751 amino acids ($AAP_{751}$), the other contains 770 ($AAP_{770}$).

Each of the three precursors used contain a transmembrane domain. When the native AAP protein is produced, it is thought to be partially secreted out of the cell. Three contiguous lysine residues at the C-terminal of the transmembrane domain effectively serve as a cytoplasmic anchor, preventing full secretion of the molecule.

The cDNA for each of the three forms of the AAP protein is obtainable from readily available sources using techniques well known in the art. The teachings of Kang, (Nature, Vol. 325, Feb. 19, 1987, pp. 733–736), Ponte, (Nature, Vol. 331, Feb. 11, 1988, pp. 525–527), and Kitaguchi, (Nature, Vol. 331, Feb. 11, 1988, pp. 530–532) provide information which allows one having ordinary skill in the art to isolate cDNAs encoding the three forms of the AAP respectively. These cDNAs can be used by one having ordinary skill in the art, using standard techniques, to produce purified AAP protein or modified AAP protein encoded by genetically altered AAP cDNA.

In the preferred embodiment of the present invention, a modification of the DNA encoding AAP is made at a codon C-terminal to the amyloid $\beta$-protein region and N-terminal to the cytoplasmic anchor region. This modification functionally deletes the cytoplasmic anchor and produces a truncated form of AAP. The modification of the three forms of AAP does not alter the regions which give rise to the variation found among the three. By modifying the AAPs, greater yield can be achieved when producing them by recombinant means. The modified AAPs used in the preferred embodiment are referred to as $AAP_{695}/s$, $AAP_{751}/s$, and $AAP_{770}/s$.

In the preferred embodiment of the present invention, immobilized amyloid, $AAP_{695}/s$, is placed in contact with the EMP, heparan sulfate proteoglycan (HSPG). The preferred embodiment provides a method to identify compounds useful to treat patients suffering from Alzheimer's disease. Relative to $AAP_{751}$ and $AAP_{770}$, $AAP_{695}$ is the predominant form of AAP associated with brain tissue. Using parallel assays with $AAP_{751}/s$ and $AAP_{770}/s$ as immobilized amyloids, compounds can be identified which specifically affect the affinity between $AAP_{695}$ and HSPG.

To practice the preferred embodiment of the present invention, $AAP_{695}/s$ is fixed in the wells of a 96 well microtiter dish. Similarly, $AAP_{751}/s$ and $AAP_{770}/s$, respectively, are fixed in wells of 96 well microtiter dishes. HSPG is added to the wells and simultaneously, stepwise dilutions of test compound are added to the wells. The dilutions cover a range of concentrations. As a control, HSPG without test compound is added to wells to determine the level of binding in the absence of the test compound. After a period of incubation sufficient to allow AAP-HSPG binding, the wells are washed to remove unbound HSPG. Anti-HSPG antibodies are then used to detect the presence of HSPG bound to AAP and to quantify the amount of HSPG bound. By analyzing the data generated by the series of dilutions of test compounds and the controls using each of the three AAP forms as immobilized amyloid, the effect of test compounds at varying concentrations upon the affinity between the respective AAP forms and HSPG can be quantitatively determined.

The example presented here is illustrative in nature and not meant to limit the scope of the present invention. The present invention provides a method for identifying compounds which affect the binding affinity between amyloid proteins and EMPs. The preferred embodiment of the present invention comprises immobilized AAP as the amyloid protein, free HSPG as the EMP, and the use of anti-HSPG antibodies to detect AAP-HSPG binding. Alternative embodiments and contemplated equivalents include methods employing different amyloid proteins, fragments of amyloid proteins, different EMPs, fragments of EMPs, the alternate use in immobilized or free entity states of these various amyloid proteins and EMPs, and the use of alternative means of amyloid protein EMP binding. Contemplated equivalents of the present invention include a method using immobilized EMP contacted with free amyloid. In this embodiment, anti-amyloid antibodies are used to evaluate qualitatively and quantitatively a test compound's capacity to modulate the affinity of amyloid to amyloid which is necessary for the accumulation of amyloid associated with the formation of amyloid plaques. Thus, using this embodiment, drugs can be developed which modulate the binding of amyloid to amyloid thereby either preventing or reducing the accumulation of amyloid which leads to plaque formation. The method can thus be used to identify compounds which interfere with plaque formation by immobilizing amyloid with either immobilized molecules that bind to it or by immobilizing it directly to a surface using other means well known in the art. Similarly, using techniques well known in the art, the detection of binding between immobilized amyloid and free amyloid can be accomplished.

EXAMPLE 1

An assay is described here which was developed to identify compounds useful for treating AD-related amyloidosis. The assay comprised immobilizing $AAP_{695}/s$ which was then exposed to free HSPG in the absence or presence of test compounds. Other aspects of the assay included exposing free HSPG to either immobilized $AAP_{751}/s$, or $AAP_{770}/s$, each in the absence or presence of test compounds. The assay was also performed with fibronectin as the immobilized protein in order to provide a positive control. In each case, a series of concentrations of HSPG and test compounds was used. Additionally, to determine whether or not the carbohydrate moiety of HSPG was involved in the binding to immobilized components, the carbohydrate moiety of HSPG was removed and assays were performed using the carbohydrate-free HSPG core protein. The test compounds used in experiments described here include heparin, dextran sulfate, chondroitin sulfate, dermatan sulfate, fibronectin, gelatin, bovine serum albumin (BSA), $Ca^{++}$ ($CaCl_2$), $Mg^{++}$ ($MgCl_2$), $Mn^{++}$ ($MnCl_2$), $Co^{++}$ ($Co(NO_3)_2$), and $Zn^{++}$ ($ZnCl_2$).

The starting materials used in this assay are readily available to one having ordinary skill in the art.

Fibronectin (from bovine plasma), heparin (grade II from porcine intestinal mucosa, average molecular weight=25,000 kDa), heparan sulfate, chondroitin sulfate, dextran sulfate, BSA, and alkaline phosphatase substrate were obtained from Sigma, St. Louis, Mo. Alkaline phosphatase conjugated goat anti-rabbit IgG was obtained from Boehringer-Manneheim, and heparitinase from ICN Biochemicals.

Low density HSPG was purified from the Engelbreth-Holm-Swarm tumor as described previously by Ledbetter et al., Biochemistry, 26, pp. 988–995 (1987). The HSPG core protein was prepared by treatment of the purified proteoglycan with heparitinase in the presence of protease inhibitors according to the method described by Kato and colleagues (Kato et al., Anal. Biochem. 148, pp. 479–484 (1985)), followed by purification on a Sepharose Cl-4B column. The purified core protein yielded a doublet on SDS-PAGE with a molecular weight of circa 400 kDa.

The intact HSPG was used to immunize rabbits, and the antibodies obtained were affinity purified through an HSPG-Sepharose column. These antibodies were found to be specific to the core protein, and did not react with the carbohydrate side chains.

C-terminally truncated $AAP_{695}/s$, $AAP_{751}/s$, and $AAP_{770}/s$ were produced by recombinant expression in insect cells as recombinant baculoviruses. The AAP cDNAs were obtained from readily available sources using techniques well known to those having ordinary skill in the art. These cDNAs were mutated at a Val codon, two positions C-terminal to the 42-amino acid β-protein domain. This functionally deleted the 56 C-terminal amino acids containing part of the transmembrane domain and the entire cytoplasmic domain, but maintained the entire extracellular portion of the AAP including the "Kunitz" protease inhibitory domains in the $AAP_{751}$ and $AAP_{770}$ forms, plus the entire β-protein sequence. This mutation enabled expression of higher levels and recovery of AAP protein, likely due to constitutive secretion in the baculovirus expression system. We therefore refer to these recombinant proteins as $AAP_{695}/s$, $AAP_{751}/s$ and $AAP_{770}/s$. Any of the three forms of the AAP gene are also readily obtained from natural sources by those having ordinary skill in the art using well known techniques. Modification of the cDNA to produce DNA which encodes the modified secretable protein was performed using standard techniques well known in the art. Recombinant baculovirus expression systems are commercially available (Invitron, San Diego, Calif.). Production and purification of modified AAP using mutated AAP cDNAs expressed in baculovirus expression systems can be performed using techniques well known to those having ordinary skill in the art. The proteins employed in these studies were homogeneous as determined by silver staining of SDS-polyacrylamide gels, by N-terminal sequencing, and by amino acid composition analyses.

To study the interaction between HSPG and either $AAP_{770}/s$, $AAP_{751}/s$, $AAP_{695}/s$ or fibronectin, the AAP proteins and fibronectin were individually immobilized on polystyrene wells and incubated with increasing concentrations of purified HSPG. Fibronectin was used as a test protein because of its known affinity for HSPG. Since fibronectin as well as all three forms of AAP bound strongly to HSPG, it was important to determine whether these interactions were occurring through the carbohydrate or protein core moieties, or perhaps both. To address this concern, the purified protein core of HSPG in place of the intact proteoglycan was utilized to examine the role of the protein component. Since antibodies to HSPG were shown to recognize the core protein with a sensitivity equal to that of the intact HSPG, this antibody was employed in the assay system when using the core protein.

The assay used in studying the interaction between HSPG and protein ligands was an ELISA technique.

Briefly, polystyrene micro-titer plates (Linbro, Flow Lab Inc.) were coated with a 100 µl solution, containing 1 µg/ml of the protein of interest (one of the three forms of AAP or fibronectin) in 20 mM NaHCO$_3$ buffer pH 9.6. After incubation overnight at 4° C., the plates were rinsed with 0.15M NaCl, 20 mM Tris-Cl pH 7.5 (TBS). The plates were then incubated with 150 µl of 1% BSA in TBS for 2 hours at 37° C. to block the residual hydrophobic surface on the wells. After rinsing with TBS containing 0.05% (w/v) Tween 20 (TBS-Tween), 100 µl of various concentrations of HSPG in TBS-Tween were added. The plates were left overnight at 4° C., to permit maximum binding of HSPG to the coated proteins. The plates were then washed extensively and incubated for 2 hours at 37° C., with 100 µl of anti-HSPG diluted in TBS-Tween containing 0.1% BSA. The plates were washed again and incubated for another 2 hours with 100 µl of goat anti-rabbit-IgG conjugated with alkaline phosphatase (1:2000 dilution) in TBS-Tween containing BSA as above. Finally, after further washing, the bound antibodies were detected by adding an alkaline phosphatase substrate solution (100 µl) containing 2 mg/ml p-nitrophenyl phosphate, 0.1 mM ZnCl$_2$, 1 mM MgCl$_2$ and 100 mM glycine pH 10. The plates were left at room temperature for 15-120 minutes depending on the protein tested. The enzyme reaction was stopped by addition of 50 µl of 2M NaOH. The absorbance of the released p-nitrophenol was measured at 405 nm with a Titertek Multiscan/MCC 340 (Flow Lab. Ltd.). The amounts of HSPG bound were determined by the net OD$_{405}$ after substracting the OD from the blank wells in which the HSPG incubation step was omitted. When the actual amounts of HSPG bound were to be calculated, a set of standards (0.05-50 ng/well) of HSPG in NaHCO$_3$ buffer were pre-coated into wells on the same plates as the test proteins. The incubations proceeded as described above omitting the incubation of the HSPG solution with the HSPG standard coated wells. The actual amounts of HSPG bound to the test proteins were calculated from the OD$_{405}$ standard curve produced by the HSPG standards using a Titersoft II E.J.A. software program (Flow Lab. Ltd.).

A set of controls using BSA coated wells was also included in all experiments. In all cases the binding of HSPG to BSA in comparison to the tested proteins was negligible.

The binding affinity of the protein-HSPG complex can be characterized by the dissociation constant (Kd) of the complex.

To determine the Kd of the protein-HSPG complex, the binding data were analyzed assuming a thermodynamic equilibrium for the formation of the complex, B, from the ligand in solution, HSPG, and the uncomplexed protein adsorbed to the microtiter well, R, according to the equation:

$$Kd = \frac{[R][HSPG]}{[B]} \quad \text{Equation 1}$$

Due to the nature of the experimental design, nonspecific binding could not be measured directly. Rather, the experimental data were corrected mathematically for the sporadic and always modest nonspecific binding by postulating that it is directly proportional to HSPG. Finally, in some experiments a minute correction was introduced to account for the background at HSPG=0. Thus, the experimentally measured quantity B$_{exp}$ was analyzed as a function of HSPG in terms of the equation:

$$B_{exp} = B_o + S[HSPG] + \frac{[B_{max}][HSPG]}{[HSPG] + Kd} \quad \text{Equation 2}$$

where B$_o$ is the slight background absorbance of the plates in the absence of HSPG, B$_{max}$ is the total binding capacity, and S is the proportionality constant for nonspecific binding. Accordingly, the experimental B$_{exp}$ vs HSPG data were analyzed using a nonlinear least squares program in order to determine the best values for the parameters in the above equation. In addition to the above mathematical model, a number of other reaction schemes were also tested by the nonlinear least squares method. It was found that the simple equilibrium model gave a fit superior to all other tested models, such as two site binding, cooperative binding, and single site binding without nonspecific binding. In a typical experiment using AAP$_{751}$/s, it was found that the analysis yields B$_o$ equivalent to 0.022±0.007 ng HSPG as compared to B$_{max}$=15.9±0.2 ng HSPG, Kd=5318±140 ng protein/ml, and S<0.0001 ml. Because of the insignificance of the value of S with respect to the experimental error, on the value of B$_{exp}$ the final analysis of this particular data set was performed using the above equation without the term corresponding to the nonspecific binding.

Data demonstrate that HSPG binds to each of the three forms of AAP, as well as to fibronectin, in a concentration dependent and saturable fashion. Binding of HSPG could be demonstrated with this assay when the concentration of HSPG used in the incubation was as low as 10 ng/ml.

Table I provides the binding affinity data expressed as Kd for either AAP$_{695}$, AAP$_{751}$, AAP$_{770}$ or fibronectin complexed with either intact HSPG or HSPG core protein in the absence of test compounds. These data served as a standard of binding affinity for experiments using testing compounds.

Quantitative analysis of binding data indicated that the binding is a single step reversible equilibrium and that one single class of binding sites exists on each of AAP$_{695}$/s, AAP$_{751}$/s, and AAP$_{770}$/s. The average of the individual dissociation constants from at least 5 individual experiments were calculated to be respectively, 0.88 nM, 10.17 nM and 9.13 nM. Similar analyses for the binding of HSPG to fibronectin (Table I) provided a Kd of 0.98 nM which is consistent with values already in the literature.

The data indicate that a high affinity exists between the HSPG and the AAPs. The data are most consistent with a simple equilibrium model involving a single AAP binding site. The Kd for this binding site was of the order of 0.9 nM when using AAP$_{695}$/s and 9-10 nM with AAP$_{751}$/s and $_{770}$/s. These observations suggest that the presence of the "Kunitz" protease inhibitor domain reduces the affinity of AAPs for HSPG possibly through steric hindrance and/or conformational alterations. The use of fibronectin provided a protein known to bind HSPG and to which binding data with AAPs could be compared. The data obtained on the binding of the HSPG core protein to fibronectin provided a Kd (0.81 nM) similar to that recently reported (2 nM) (Foncin, J. F., Nature 326, p. 136 (1987)). The binding of intact HSPG to fibronectin occurs with a similar affinity (Kd=0.98 nM).

Heparin and dextran sulfate, respectively, were each used as test compounds to determine their effect on the HSPG binding to AAP forms and fibronectin. Various concentrations of heparin or dextran sulfate were added together with a constant amount of HSPG to wells coated with AAPs for fibronectin. Table II shows that both these polysaccharides inhibited HSPG binding to AAP$_{695}$/s more strongly than to AAP$_{751}$/s or fibronectin. Dextran sulfate at 32 µg/ml inhibited about 85% of HSPG's binding to AAP$_{695}$/s, whereas it inhibited HSPG binding to AAP$_{751}$/s or fibronectin by only 30%. Increasing the concentrations of dextran sulfate to 500 mg/ml did not further decrease the degree of HSPG binding to AAP$_{751}$/s or fibronectin. Likewise, 62.5 µg/ml heparin inhibited HSPG binding to AAP$_{695}$/s by 75%, but even at 4000 µg/ml, heparin only inhibited HSPG binding to AAP$_{751}$/s by 25% and to fibronectin by 45%. Heparin at 400 µg/ml could reduce the HSPG affinity for AAP-695/s by a factor of 5-10.

Having shown that the binding of HSPG to AAPs is inhibited by both heparin and dextran sulfate, it was important to determine whether these effects were mediated by the HSPG core protein. AAP$_{751}$/s and AAP$_{695}$/s were incubated with varying concentration of the HSPG core protein in parallel with experiments utilizing the intact proteoglycan. The results, shown in Table I, indicate that the heparitinase-treated HSPG binds to the AAPs and to fibronectin with Kd's very similar to those determined using the intact protein. This indicates that the high affinity HSPG binding site is constituted by the polypeptide chain, rather than the glycosaminoglycan (GAG) side chains.

Data from assays using either AAP$_{695}$/s and AAP$_{751}$/s, respectively, with intact HSPG or HSPG core protein, respectively, in the presence of a fixed concentration of heparin (400 µg/ml) demonstrate the specific effectiveness of heparin on the binding affinity of AAP$_{695}$ to either form of HSPG. In the case of AAP$_{695}$/s, the Kd of intact HSPG increased approximately four-fold from 0.9±0.25 nM in the absence of heparin to 3.56±1.78 nM in its presence. Using the core protein, the corresponding Kd's increased approximately ten-fold, from 0.90±0.52 nM to 10.12±3.35 nM respectively. The Ki for heparin can thus be calculated from the relationship: Kd$_{app}$=Kd$_{con}$ (1+[I]/Ki), where Kd$_{app}$ is the Kd calculated in the presence of heparin, Kd$_{con}$ is the Kd calculated in the absence of heparin, and [I] is the heparin concentration. The Ki is thus calculated to be on the order of 5.5 µM for the intact HSPG, and 1.6 µM for the HSPG core protein. These interactions are clearly less avid than the binding of HSPG to AAP$_{695}$/s. No such effect was seen when using AAP$_{751}$/s.

Other sulfated GAGs were also tested. Neither dermatan sulfate nor chondroitin sulfate, even at concentrations of 4000 µg/ml, had any effect on HSPG binding to any AAP protein tested.

Both intact HSPG and HSPG core protein bound to the AAPs with similar affinities. Dextran sulfate and heparin interfered with total binding of HSPG to all three of the AAPs. Data show that inhibition is probably competitive for the binding of HSPG to AAP$_{695}$/s, but noncompetitive for the AAP$_{751}$/s or fibronectin. Accordingly, Kd's were affected only for AAP$_{695}$/s in the presence of heparin. In this latter case, the calculated Ki's were over three orders of magnitude higher than the corresponding Kd's. Thus, while a qualitative difference exists between the binding of HSPG to AAP$_{695}$/s relative to AAP$_{751}$/s and AAP$_{770}$/s, interactions between the protein cores are clearly responsible for the high affinity binding in all cases. This was expected from the similar Kd's of the AAPs for the intact HSPG and its core protein.

In addition to test compounds described above, other compounds were tested to determine their effect upon HSPG-AAP binding. Table III summarizes the effects of various test compounds on the binding of intact HSPG to AAP$_{695}$, AAP$_{751}$, and fibronectin. While excess fibronectin in solution (50 µg/ml) competes with the binding of HSPG to immobilized fibronectin as expected (a 65% inhibition) it only moderately interferes with HSPG binding to the AAPs. Gelatin, (50 µg/ml) which does not bind to HSPG, inhibits HSPG binding to AAP$_{751}$/s, AAP$_{695}$/s and fibronectin by 40%, 50% and 70% respectively. HSPG binding was unaffected by various divalent metal ions including Ca$^{++}$ (3 mM), Mg$^{++}$ (10 mM), Mn$^{++}$ (4 mM), and Co$^{++}$ (0.1 mM). Only Zn$^{++}$ (0.1 mM) showed an inhibitory effect and this was more pronounced for AAP$_{695}$/s (70% inhibition) than for AAP$_{751}$/s or fibronectin (31% and 55% inhibitions respectively).

Results clearly show qualitative differences in binding of HSPG to AAP$_{695}$/s, as compared with binding to the AAP forms which contain the "Kunitz" protease inhibitor domain. Firstly, HSPG binds more avidly to AAP$_{695}$/s than to AAP$_{751}$/s or AAP$_{770}$/s. Secondly, effects of Zn$^{++}$, dextran sulfate and heparin on HSPG binding are more pronounced with AAP$_{695}$/s than with AAP$_{751}$/s.

In summary, results indicate that highly specific interactions between intact AAPs and HSPG, both of which are components of neuritic plaques. The binding affinity of AAP$_{695}$ is at least as avid as HSPG's interactions with fibronectin. These interactions may be an initial step in the genesis of the characteristic Alzheimer's lesions. Using the assay described here, the effect that compounds have on the interaction between HSPG and each of the three forms of AAP respectively can be determined. Thus, compounds can be identified which specifically modulate the interaction of AAP$_{695}$ to HSPG, thereby impairing a postulated initiation step to amyloid deposition in the brain tissue of Alzheimer's patients. The results here demonstrate that heparin and dextran sulfate specifically modulate the HSPG-AAP$_{695}$ affinity. The assay described here can be used to test and identify other compounds with similar modulatory effects.

TABLE I

| Summary of Kd's for Intact and Core Protein of HSPG | | |
|---|---|---|
| Protein Used | Intact HSPG | Core Protein |
| Fibronectin | 0.98 ± 0.10 nM (5)* | 0.81 ± 0.12 nM (4) |
| AAP$_{695}$/S | 0.88 ± 0.35 nM (7) | 0.90 ± 0.53 nM (3) |
| AAP$_{751}$/S/ | 10.17 ± 2.45 nM (9) | 7.61 ± 2.05 nM (3) |
| AAP$_{770}$/S | 9.13 ± 1.06 nM (6) | n.d. |

Values are the means ± SD
*Numbers in parentheses indicates number of experiments done.

TABLE II

| | Fibronectin | AAP$_{751}$ | AAP$_{695}$ |
|---|---|---|---|
| Effect of Heparin on HSPG Binding | | | |

TABLE II-continued

|  | Fibronectin | AAP751 | AAP695 |
|---|---|---|---|
| Control | 100% | 100% | 100% |
| Heparin 31.2 μg/ml | 93 | 89 | 29 |
| 62.5 | 91 | 75 | 26 |
| 125 | 73 | 84 | 16 |
| 250 | 85 | 82 | 10 |
| 500 | 79 | 54 | 7 |
| 1000 | 79 | 60 | 3 |
| 2000 | 77 | 53 | 2 |
| 4000 | 74 | 58 | 1 |
| Effect of Dextran Sulfate on HSPG Binding | | | |
| Control | 100% | 100% | 100% |
| Dextran Sulfate 31.2 μg/ml | 67 | 74 | 14 |
| 62.5 | 70 | 71 | 11 |
| 125 | 68 | 67 | 9 |
| 250 | 63 | 68 | 11 |
| 500 | 60 | 63 | 11 |

TABLE III

Effect of Various Effectors on the Binding of Intact HSPG to Amyloid Precursor Proteins and Fibronectin[a].

| Additions | Activity[b] AAP751/S | AAP695/S | Fibronectin |
|---|---|---|---|
| None (control) | 100 | 100 | 100 |
| Dextran sulfate 500 μg/ml | 63 ± 8.6 | 8.5 ± 2.4 | 71 ± 10.8 |
| Heparin 500 μg/ml | 69 ± 12 | 10.2 ± 5.2 | 71.7 ± 4.9 |
| Dermatan sulfate 4 mg/ml | 127 ± 30 | 121 ± 14 | 107 ± 20.6 |
| Chondroitin sulfate 4 mg/ml | 110 ± 24.2 | 110 ± 15.3 | 107 ± 10.8 |
| Fibronectin 50 μg/ml | 103.7 ± 14.5 | 76.3 ± 9.5 | 33.4 ± 18.4 |
| BSA 50 μg/ml | 113.8 ± 22.1 | 102.8 ± 7.6 | 108 ± 6.4 |
| Gelatin 50 μg/ml | 60.2 ± 8.3 | 50.5 ± 18.4 | 28.5 ± 16.5 |
| $CaCl_2$ 4 mM | 105.5 ± 3.5 | 92.5 ± 7.7 | 101.5 ± 2.1 |
| $MgCl_2$ 10 mM | 102.5 ± 7.8 | 102.5 ± 6.4 | 105 ± 9.9 |
| $MnCl_2$ 4 mM | 106 ± 19.7 | 107 ± 18.3 | 101.5 ± 9.2 |
| $ZnCl_2$ 0.1 mM | 85.5 ± 9 | 31 ± 8.1 | 44 ± 14.6 |
| Co($NO_3$) 0.1 mM | 91 ± 8.5 | 97.3 ± 2.5 | 100 ± 14 |

[a]Bindings were performed at constant HSPG protein concentrations of 2 μg/ml.
[b]Activities are expressed as percentage ± SD of control in the absence of any added effector. Three experiments were performed when examining each metal. All other experiments were done in quadruplicate.

We claim:

1. A method for identifying compounds useful for altering binding of heparan sulfate proteoglycan (HSPG) to an amyloid protein comprising the steps of:
   a) performing a first assay comprising the steps of:
      i) contacting a known quantity of amyloid protein with a known quantity of HSPG in the presence of a test compound;
      said amyloid protein selected from the group consisting of: β-protein associated with Alzheimer's Disease, Down's Syndrome, HCHWA-Dutch type, Guamanian Parkinsonian Dementia Complex and normal aging; the several forms of Alzheimer's precursor protein (AAP: AAP695, AAP751, and AAP770); Amyloid A (AA), the amyloid associated with inflammation; IAPP, the amyloid associated with adult onset diabetes; prion amyloids, the amyloids associated with Gerstmann Straussler Syndrome and Creutzfeldt-Jakob disease; transthyretin amyloid, the amyloid associated with familial amyloidotic polyneuropathy; and cystatin C, the amyloid associated with Icelandic type familial heredity cerebral hemorrhage with amyloid, HCHWA Icelandic type; and
      (ii) determining the affinity of said amyloid protein to said HSPG contacted in the presence of said test compound;
   b) performing a second assay comprising the steps of:
      i) contacting said known quantity of said amyloid protein with said known quantity of said HSPG in the absence of said test compound;
      ii) determining the affinity of said amyloid protein to said EMP contacted in the absence of said test compound;
   c) comparing the affinity of said amyloid protein to said HSPG contacted in the presence of said test compound to the affinity of said amyloid protein to said HSPG contacted in the absence of said test compound.

2. A method according to claim 1 wherein said amyloid protein is immobilized upon a solid phase.

3. A method according to claim 2 wherein affinity of said HSPG to immobilized amyloid is determined by the steps of:
   a) contacting said HSPG with said immobilized amyloid in the presence or absence of said test compound for a sufficient time to allow binding said HSPG to said immobilized amyloid;
   b) washing said immobilized amyloid to remove any unbound HSPG;
   c) contacting said immobilized amyloid with antibodies specific for said HSPG; and
   d) measuring the quantity of HSPG bound to amyloid by measuring the quantity of said antibodies present.

4. A kit for practicing a method for identifying compounds useful for altering binding of heparan sulfate proteoglycan (HSPG) to an immobilized amyloid protein, said kit comprising:
   a) a first container having amyloid protein immobilized upon the inner surface;
   b) a second container which contains HSPG dissolved in solution;
   c) a third container which contains antibodies specific for HSPG, said antibodies dissolved in solution; and
   d) a fourth container which contains labelled antibodies specific for antibodies specific for HSPG, said labelled antibodies dissolved in solution.

* * * * *

UNITED STATES PATENT OFFICE
CERTIFICATE OF CORRECTION

Patent No.     5,164,295     Dated     November 17, 1992

Inventor(s)    Robert Kisilevsky, et al.

It is certified that error appears in the above-identified patent and that said Letters Patent is hereby corrected as shown below:

On the Title page, item [75]
Inventors should read:

Robert Kisilevsky; Walter A. Szarek; Suree Narindrasorasak, all of Kingston, Canada; Ferenc J. Kezdy; Barry D. Greenberg, both of Kalamazoo, Michigan.

Signed and Sealed this

First Day of February, 1994

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,164,295
DATED : November 17, 1992
INVENTOR(S) : Robert Kisilevsky, et al It is certified that error appears in the above-indentified patent and that said Letters Patent is hereby corrected as shown below:

On the Title Page, Item [73]

The Upjohn Company, Kalamazoo, Mich., and Queen's University Kingston, Canada.

Signed and Sealed this

Nineteenth Day of April, 1994

Attest:

BRUCE LEHMAN

*Attesting Officer*  *Commissioner of Patents and Trademarks*